United States Patent
Bolam et al.

(10) Patent No.: US 7,850,152 B2
(45) Date of Patent: Dec. 14, 2010

(54) METHODS AND DEVICES FOR MOISTURIZING HYPERPOLARIZED NOBLE GASES AND ASSOCIATED MOISTURIZED PHARMACEUTICAL GRADE INHALABLE HYPERPOLARIZED GAS PRODUCTS

(75) Inventors: Ken Bolam, Raleigh, NC (US); Patrick Cella, Raleigh, NC (US); John Nouls, Raleigh, NC (US); Brian Teixeira, Cary, NC (US)

(73) Assignee: Medi Physics, Inc., Princeton, NJ (US)

( * ) Notice: Subject to any disclaimer, the term of this patent is extended or adjusted under 35 U.S.C. 154(b) by 0 days.

(21) Appl. No.: 10/128,048

(22) Filed: Apr. 23, 2002

(65) Prior Publication Data

US 2002/0168419 A1 Nov. 14, 2002

Related U.S. Application Data

(60) Provisional application No. 60/285,973, filed on Apr. 24, 2001.

(51) Int. Cl.
*B01F 3/04* (2006.01)
(52) U.S. Cl. .............. 261/127; 261/104; 261/121.1; 261/142; 128/203.12; 128/203.26
(58) Field of Classification Search ........... 261/127, 261/142, 154, 99, 104, 107, 121.1; 128/203.12, 128/203.16, 203.17, 203.26, 203.27, 204.13, 128/204.17
See application file for complete search history.

(56) References Cited

U.S. PATENT DOCUMENTS

| | | | |
|---|---|---|---|
| 3,903,883 A | | 9/1975 | Froehlrich et al. |
| 4,200,094 A | | 4/1980 | Gedeon |
| 4,355,636 A | * | 10/1982 | Oetjen et al. ........... 128/204.13 |
| 4,381,267 A | * | 4/1983 | Jackson ........................ 261/104 |
| 4,657,713 A | * | 4/1987 | Miller .......................... 261/142 |
| 4,921,642 A | * | 5/1990 | LaTorraca ..................... 261/142 |
| 4,969,998 A | * | 11/1990 | Henn ........................... 210/490 |
| 5,148,801 A | * | 9/1992 | Douwens et al. ........ 128/203.16 |
| 5,545,396 A | | 8/1996 | Albert et al. .................... 424/93 |
| 5,617,913 A | * | 4/1997 | DeGregoria et al. ... 165/104.11 |
| 5,642,625 A | | 7/1997 | Cates, Jr. et al. ............. 62/55.5 |
| 5,809,801 A | | 9/1998 | Cates, Jr. et al. .............. 62/637 |
| 5,976,220 A | * | 11/1999 | Braun et al. .................... 95/45 |

(Continued)

FOREIGN PATENT DOCUMENTS

EP  0265163  4/1988

(Continued)

OTHER PUBLICATIONS

Dosch, The Anesthesia Gas Machine, Vaporizers, Compressed Gases, Safety: Avoiding the Pitfalls, URL ourworld.cs.com/ht a/dosch m/part1.htm (© May 28, 2000) 30 pps.

(Continued)

*Primary Examiner*—Scott Bushey
(74) *Attorney, Agent, or Firm*—Robert F. Chisholm

(57) ABSTRACT

Methods and devices for moisturizing hyperpolarized noble gas and associated hyperpolarized noble gas products which are formulated for inhalation or ventilation delivery include adding moisture content to (dry) hyperpolarized gas.

9 Claims, 5 Drawing Sheets

U.S. PATENT DOCUMENTS

| | | | |
|---|---|---|---|
| 6,062,212 A | 5/2000 | Davison et al. | 128/200.16 |
| 6,079,213 A | 6/2000 | Driehuys et al. | 62/3.1 |
| 6,199,385 B1 | 3/2001 | Driehuys et al. | 62/51.1 |
| 6,237,363 B1 * | 5/2001 | Zollinger et al. | 62/600 |
| 6,488,910 B2 * | 12/2002 | Driehuys | 424/9.3 |
| 6,667,008 B2 * | 12/2003 | Zollinger et al. | 422/83 |
| 6,769,431 B2 * | 8/2004 | Smith et al. | 128/203.16 |

FOREIGN PATENT DOCUMENTS

| | | |
|---|---|---|
| WO | WO98/30918 | 7/1998 |

OTHER PUBLICATIONS

Mugler, III et al, "MR Imaging and Spectroscopy Using Hyperpolarized 129Xe Gas: Preliminary Human Results," 37 Magn. Reson. In Med., vol. 37, No. 6, pp. 809-815 (1997).

Schearer, "Optical Pumping of Neon ($^3P_2$) Metastable Atoms," Phys. Rev., vol. 180, No. 1, pp. 83-90 (1969).

International Search Report fr PCT/US02/12820.

* cited by examiner

METHODS AND DEVICES FOR MOISTURIZING HYPERPOLARIZED NOBLE GASES AND ASSOCIATED MOISTURIZED PHARMACEUTICAL GRADE INHALABLE HYPERPOLARIZED GAS PRODUCTS

RELATED APPLICATIONS

This application claims priority from U.S. Provisional Application Ser. No. 60/285,973, filed Apr. 24, 2001, the contents of which are hereby incorporated by reference as if recited in full herein.

FIELD OF THE INVENTION

The present invention relates to magnetic resonance imaging ("MRI") and NMR spectroscopy using hyperpolarized noble gases.

BACKGROUND OF THE INVENTION

Conventionally, MRI has been used to produce images by exciting the nuclei of hydrogen molecules (present in water protons) in the human body. However, it has been discovered that polarized noble gases can produce improved images of certain areas and regions of the body which have heretofore produced less than satisfactory images in this modality. Polarized Helium 3 ("$^3$He") and Xenon-129 ("$^{129}$Xe") have been found to be particularly suited for this purpose. See U.S. Pat. No. 5,545,396 to Albert et al., entitled *Magnetic Resonance Imaging Using Hyperpolarized Noble Gases*, the disclosure of which is hereby incorporated by reference herein as if recited in full herein.

In order to obtain sufficient quantities of the polarized gases necessary for imaging, hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the Magnetic Resonance Imaging ("MRI") signal intensity, thereby potentially allowing physicians to obtain better images of many tissues and organs in the body.

Generally stated, in order to produce the hyperpolarized gas, the hyperpolarizer is configured such that the noble gas is blended with optically pumped alkali metal vapors such as rubidium ("Rb"). These optically pumped metal vapors collide with the nuclei of the noble gas and hyperpolarize the noble gas through a phenomenon known as "spin-exchange". The "optical pumping" of the alkali metal vapor is produced by irradiating the alkali-metal vapor with circularly polarized light at the wavelength of the first principal resonance for the alkali metal (e.g., 795 nm for Rb). Generally described, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange".

Conventionally, lasers have been used to optically pump the alkali metals. Various lasers emit light signals over various wavelength bands. In order to improve the optical pumping process for certain types of lasers (particularly those with broader bandwidth emissions), the absorption or resonance line width of the alkali metal can be broadened to more closely correspond with the particular laser emission bandwidth of the selected laser. This broadening can be achieved by pressure broadening, i.e., by using a buffer gas in the optical pumping chamber. Collisions of the alkali metal vapor with a buffer gas can lead to a broadening of the alkali's absorption bandwidth.

For example, it is known that the amount of polarized $^{129}$Xe which can be produced per unit time is directly proportional to the light power absorbed by the Rb vapor. Thus, polarizing $^{129}$Xe in large quantities generally takes a large amount of laser power. When using a diode laser array, the natural Rb absorption line bandwidth is typically many times narrower than the laser emission bandwidth. The Rb absorption range can be increased by using a buffer gas. Of course, the selection of a buffer gas can also undesirably impact the Rb-noble gas spin-exchange by potentially introducing an angular momentum loss of the alkali metal to the buffer gas rather than to the noble gas as desired. In any event, after the spin-exchange has been completed, the hyperpolarized gas is separated from the alkali metal prior to introduction into a patient.

Conventionally, gas-phase imaging has been possible hyperpolarized noble gases such as, but not limited to, $^3$He and $^{129}$Xe, each of which have been particularly useful in producing ventilation-driven (inhalation delivery) images of the lungs, a region where proton images have produced signal voids. For example, MRI images using gas-space-imaging techniques have been generated using hyperpolarized $^{129}$Xe gas. See Mugler III et al., *MR Imaging and Spectroscopy Using Hyperpolarized $^{129}$Xe gas: Preliminary Human Results*, 37 Magnetic Resonance in Medicine, pp. 809-815 (1997).

SUMMARY OF THE INVENTION

Generally stated, the present invention is directed to methods and apparatus that moisturize hyperpolarized noble gas prior to inhalation or ventilation delivery to a subject as well as related moisturized hyperpolarized noble gas products suitable for in vivo administration. In certain embodiments, the moisture is added in situ just prior to the administration to the subject.

In certain embodiments, methods of adding moisture include introducing moisture to a quantity of gaseous phase hyperpolarized noble gas to generate a moisturized gaseous hyperpolarized gas suitable for inhalation or ventilation administration to a subject. The moisturizing can be such that the hyperpolarized gas has a relative humidity of between about 5-80%, and in particular embodiments, a relative humidity of between about 10-30%.

Other embodiments are directed to apparatus for adding moisture to hyperpolarized noble gas, comprising: (a) a hyperpolarized noble gas supply source; (b) means for introducing moisture to a quantity of gaseous phase hyperpolarized noble gas in fluid communication with the hyperpolarized noble gas supply source; and (c) means for generating a moisturized pharmaceutical grade gaseous hyperpolarized noble gas product which is suitable for inhalation or ventilation administration to a subject.

Still other embodiments are directed to pharmaceutical hyperpolarized noble gas phase mixtures formulated for in vivo inhalation or ventilation administration, comprising between about 5-80% relative humidity.

In certain embodiments, the hyperpolarized noble gas mixture can be heated to be at about body temperature prior to administration to a subject.

Still other embodiments are directed to a biocompatible hyperpolarized noble gas product formulated for in vivo administration. The product comprises a quantity of hyperpolarized noble gas, a quantity of a selected mixer gas, and a moisture concentration between about 4-20 mg/L at 20° C.

The foregoing and other objects and aspects of the present invention are explained in detail herein.

DETAILED DESCRIPTION OF EMBODIMENTS OF THE INVENTION

Figure 1:
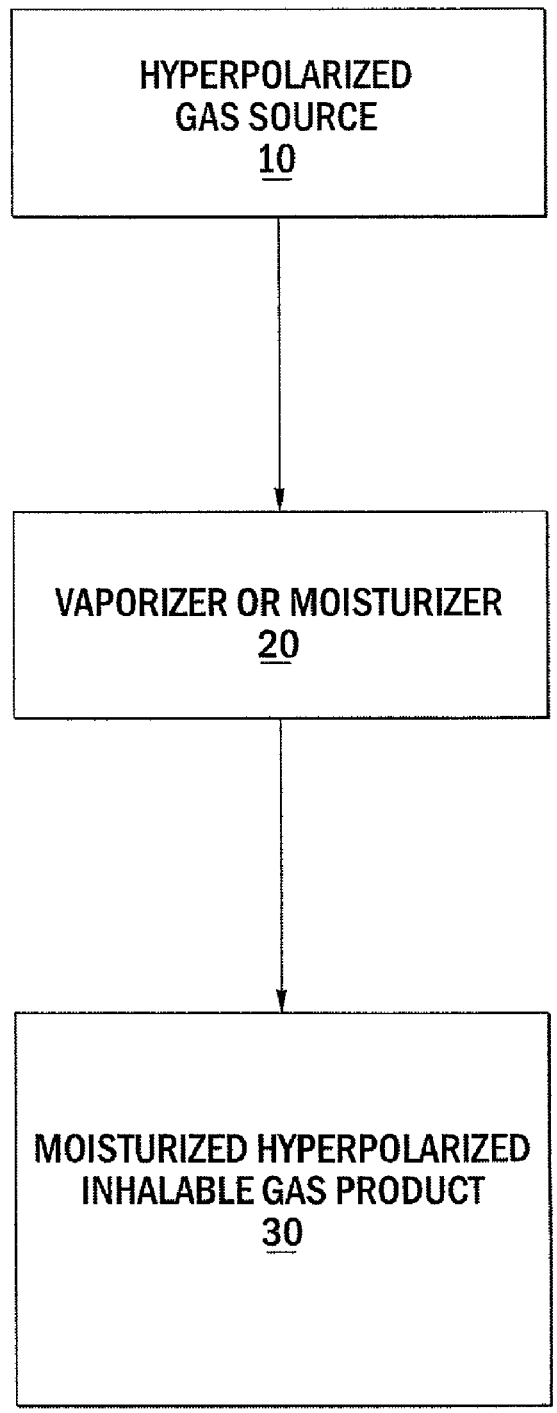
FIG. 1 is schematic diagram of operations that can be carried out according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, layers and regions may be exaggerated for clarity.

As known to those of skill in the art, polarized gases can be collected, frozen, thawed, and used in MRI or NMR spectroscopic applications. For ease of description, the term "frozen polarized gas" means that the polarized gas has been frozen into a substantially solid state. The term "liquid polarized gas" means that the polarized gas has been or is liquefied into a liquid state. Thus, although each term includes the word "gas", this word is used to identify and descriptively track the gas, which is produced via a hyperpolarizer, to obtain a polarized "gas" product. Thus, as used herein, the term "gas" may have been used in certain places to descriptively indicate a hyperpolarized noble gas product and may be used with modifiers such as "solid", "frozen", "dissolved", and "liquid" to describe the physical state or phase of that product (rather than describing the product as being in a gaseous phase). Also, for certain embodiments, the hyperpolarized gas may have been in one or more forms during production or delivery, but is processed such that it is ultimately a pharmaceutical grade gas suitable for in vivo inhalation or ventilation administration or delivery to a subject.

Various techniques have been employed to accumulate and capture polarized gases. For example, U.S. Pat. No. 5,642, 625 to Cates et al., describes a high volume hyperpolarizer for spin-polarized noble gas, and U.S. Pat. No. 5,809,801 to Cates et al. describes a cryogenic accumulator for spin-polarized $^{129}$Xe. U.S. Pat. No. 6,079,213 to Driehuys et al., entitled "Methods of Collecting, Thawing, and Extending the Useful Life of Polarized Gases and Associated Apparatus", describes an improved accumulator and collection and thaw methods. The disclosures of these documents are hereby incorporated by reference as if recited in full herein.

As used herein, the terms "hyperpolarize", "polarize", and the like mean to artificially enhance the polarization of certain noble gas nuclei over the natural or equilibrium levels. Such an increase is desirable because it allows stronger imaging signals corresponding to better MRI (and spectroscopy) images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396. Combinations of hyperpolarized and non-hyperpolarized noble gases and noble gas isotopes may also be suitable for ventilation or inhalation administration.

Generally stated, in certain embodiments, a patient is positioned in an MRI unit and exposed to a magnetic field. The MRI unit typically includes a super-conducting magnet, gradient coils (with associated power supplies), a surface coil (transmit/receive RF coil), and a RF amplifier for generating RF pulses set at predetermined frequencies. For $^{129}$Xe imaging at 1.5 T field strength, the MRI unit is set to operate in the gas-phase at about 17.6 MHz. In yet another embodiment, the imaging method employs a 17.6 MHz gas phase excitation pulse and an associated dissolved phase excitation pulse of preferably about 17.59648 MHz. Of course, the magnet field strength and excitation frequency can vary as is well known to those of skill in the art and may vary depending on the hyperpolarized gas used and the particular application thereof. In other embodiments, an NMR spectroscopy apparatus can be used and the field strength may be reduced or increased from or be similar to that used in the MR apparatus to obtain signals corresponding to the chemical shift of the administered hyperpolarized gas in the subject.

In any event, the RF pulse(s) is transmitted to the patient to excite the nuclei of the hyperpolarized noble gas (such as $^3$He or $^{129}$Xe). Generally stated, the surface coil can be tuned to a selected frequency range and positioned adjacent the targeted imaging region to transmit the excitation pulses and to detect responses to the pulse sequence generated by the MRI unit. Surface coils for standard chest imaging typically include a wrap-around coil with conductors positioned on both the front and back of the chest. Examples of acceptable coils known to those of skill in the art include a birdcage configuration, a Helmholtz pair, a surface coil, and a solenoid coil (for permanent magnets).

Conventionally, the patient or subject (typically an animal or human) inhales a (predetermined) quantity of hyperpolarized gas into the pulmonary region (i.e., lungs and trachea). In certain embodiments, after inhalation, the patient holds his or her breath for a predetermined time such as 5-20 seconds. This can be described as a "breath-hold" delivery. Examples of suitable "single dose" quantities of polarized gases for breath-hold delivery include 0.5, 0.75, and 1.0 liters of gas at desired dosages (such as 1, 5, or 9 mmol). The administration can be performed so as to deliver successive quantities of the hyperpolarized gas, either in the same or different quantities or dosages, at desired intervals during the evaluation or imaging session. For example, a 1.0 mmol dose in 0.5 liter volume may be followed by a 5 mmol dose in a 1.0 liter volume. Preferably, the dose at inhalation contains hyperpolarized gas with a polarization level above 5%, and more typically a polarization level above about 20%. Similar formulations may be used for ventilation deliveries.

As schematically shown in FIG. 1, in certain embodiments, a source of hyperpolarized gas 10 is placed in fluid communication with a moisturizer/vaporizer 20 such that, during operation, a moisturized inhalable hyperpolarized gas product 30 is produced. The addition of moisture 30M (FIG. 2) may reduce the "tickling" or dry sensation which may be felt by certain subjects during, or following, inhalation or ventilation delivery of non-moisturized polarized gas. In certain embodiments, the moisture 30M is provided by introducing water, an aqueous-based liquid composition, or a vapor to the hyperpolarized gas. In certain embodiments, the water may be formulated such that it is substantially or partially deoxygenated. In certain particular embodiments such as, for example, when limited quantities of moisture are employed, or in other desired applications, deuterated water may also be employed.

The moisturizer 20 may be configured in a number of suitable configurations that introduce moisture to the hyperpolarized gas without substantially degrading the polarization level of the hyperpolarized gas. In certain embodiments, it may be desirable to introduce the moisture to the hyperpolarized gas in situ, temporally proximate to delivery of the hyperpolarized gas to the subject.

In certain embodiments, the methods and devices of the present invention can be configured to provide a relative humidity of between about 5 and 80 percent, and preferably 10-30 percent, and more preferably about a 30 percent relative humidity level. The moisture or humidity level is selected to provide inhalation comfort or reduce discomforting tactile sensations (during and after inhalation) yet with a moisture content which is limited so as to inhibit the depolarizing influence on the hyperpolarized gas. Relative humidity (RH) can be described as the amount of moisture or liquid present in a sample, as compared to the absolute humidity possible in the sample at a temperature (expressed as a %). See Michael P. Dosch, *The Anesthesia Gas Machine, Vaporizers, Compressed Gases, Safety: Avoiding the Pitfalls*, URL our-world.cs.com/ ht a/doschm/part1.htm; gasnet.org/education/machine. Conventional anesthesia gas machine (AGM) specifications are described under ASTM F1161. Examples of different concentrations of moisture at RH values found in different artificial or natural environments include: conventional anesthesia machines which can provide about 0 mg/L at a relative humidity of 0; normal room air which has about 9 mg/L at 20° C. and 50% relative humidity; and tracheal air which at the carina can have about 44 mg/L at 37° C. and 100% relative humidity. Methods and devices of the present invention may provide corresponding and/or desired selected moisture formulations. In certain embodiments, the operations can be carried out to provide desired ranges of moisture formulations such as, for example, moisture in a gas blend for in vivo administration of between about 4-20 mg/L at 20° C.

Moisture can be added at various points in the gas processing/delivery process. The major points in the hyperpolarized gas inhalation administration process may be described as (a) polarization, (b) mixing, (c) delivery, and (d) inhalation. The following embodiments illustrate how moisture can be added to polarized gas at or between these points. In addition, the polarized gas may be heated to about body temperature (such as, but not limited to, between about 97-99° F.) during or prior to delivery (prior to contact with the subject). Various heating mechanisms can be employed to generate any suitable heat exchange actions such as, but not limited to, convection, conduction, and irradiation.

Embodiment 1

Adding Moisture to Gas Being Polarized

As noted above, one early step in the process is polarization. For a more detailed discussion of the polarization process and apparatus with the optical pumping cell, see e.g., U.S. Pat. Nos. 5,642,625, 5,809,801, 6,199,385, and co-pending co-assigned, U.S. application Ser. Nos. 09/163,721, and 09/344,000; the contents of these documents are hereby incorporated by reference as if recited in full herein. Generally described, noble gas intended for polarization is transferred into a polarization cell, typically an optical pumping chamber. Moisture can be added to the gas either before, after or during transfer into the polarization cell. If moisture is added to the spin exchange or optical pumping cell, a metastability exchange process should be employed, as the presence of alkali metal in the cell may react with the moisture and act as a scavenger, thus removing it form the gas. See e.g., Schearer L D, *Phys Rev*, 180:83 (1969); Laloe F, Nacher P J, Leduc M, and Schearer L D, AIP ConfProx #131 (Workshop on Polarized $^3$He Beams and Targets) (1984). The technique of metastability exchange involves direct optical pumping of, for example, $^3$He without need for an alkali metal intermediary. Metastability exchange optical pumping will work in the same low magnetic fields in which spin exchange pumping works. Similar polarizations are achievable, but generally at lower pressures, e.g., about 0-10 Torr.

Alternatively, the moisture can be introduced to the hyperpolarized gas at the conclusion of the polarization cycle for optically pumped spin-exchange polarization batch production (such as is typically used to produce polarized $^3$He) or downstream of the pumping cell for substantially continuous flow optically pumped spin-exchange polarization production (typically used to produce polarized $^{129}$Xe). Indeed the introduction of moisture, post-polarization, may, in certain embodiments, also be used as a leaching filter to trap of filter alkali metal residue.

Embodiment 2

Adding Moisture to the Mixing Gas

Mixing of polarized gas with a non-polarized buffer or mixing gas is a method used to regulate the polarization level for gas management utilization and/or for controlling dose concentration. The mixer or buffer gas is a medical grade gas that is biologically or physiologically compatible for in vivo administration to a subject. Examples include, but are not limited to, noble gases such as helium, nitrogen, xenon, and mixtures thereof. Moisturizing the mixing gas either before or during the mixing process is a viable means of adding moisture.

Figure 2:
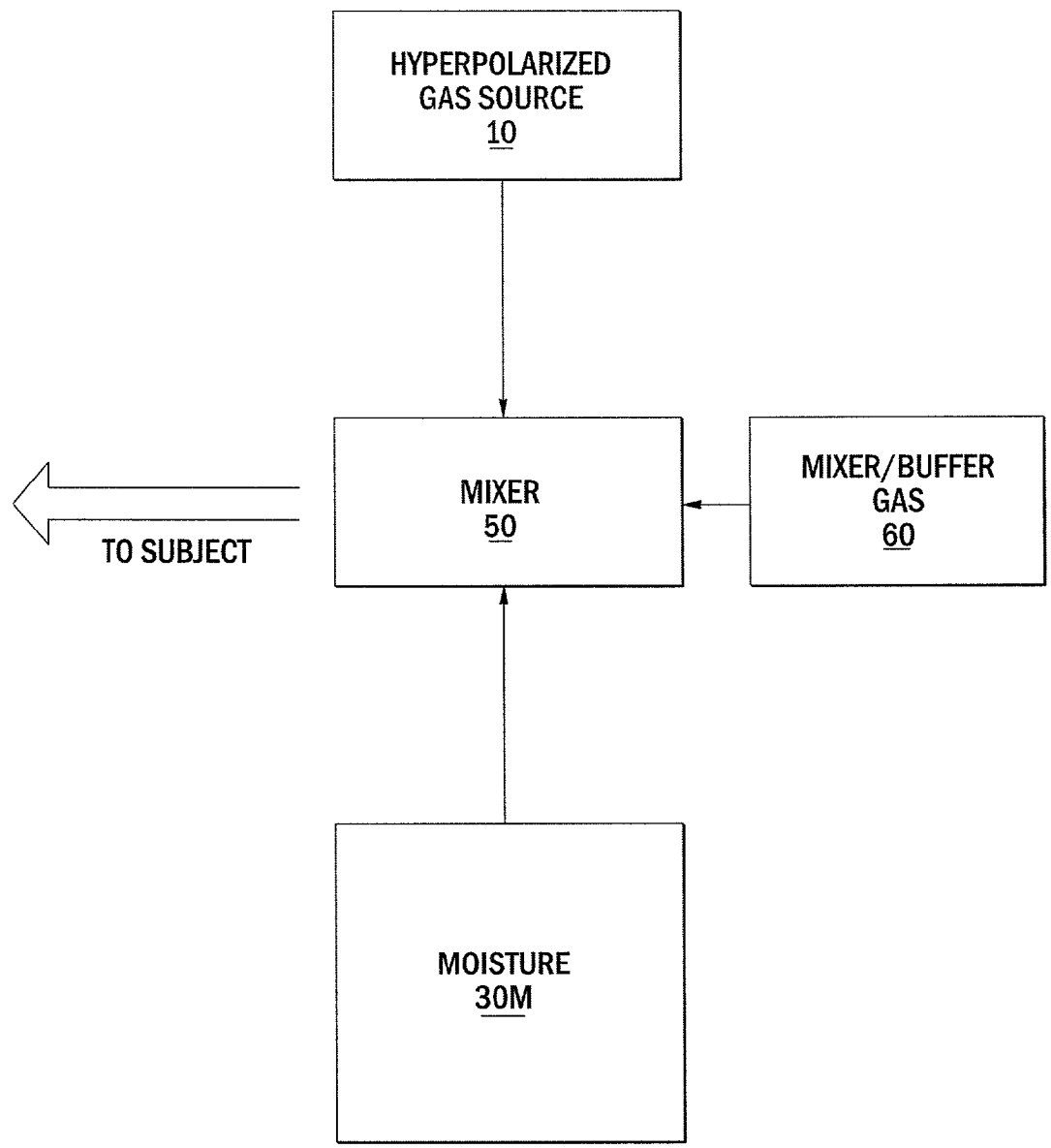
FIG. 2 is a schematic diagram of a system according to embodiments of the present invention.

FIG. 2 illustrates that the hyperpolarized gas source 10 can be directed to a mixer 50 positioned to mix the hyperpolarized gas with the mixing gas directed from the mixing gas source 60. The moisture can be introduced to the mixer 50 separately, or into the mixing gas such that the mixing gas holds the moisture prior to entry into the mixer 50. The mixing gas can be formulated or pre-mixed with a known amount of moisture, such as water, in the vapor phase. The final mix of hyperpolarized gas on the one hand, and mixing gas and moisture on the other hand, can be added in quantities or concentrations to provide the desired moisture level. For example, for the situation where the mixing gas contains a known quantity of water, adding a known volume of mixing gas to a known volume of hyperpolarized gas allows the determination of what quantity of moisture has been added to the hyperpolarized gas mixture before administration and, subsequently, may allow for correlation of the signal strength obtained during data collection and/or imaging.

Alternatively, the moisture can be added to the mixture of the mixer gas and hyperpolarized gas as it exits or travels away from the mixer 50 toward delivery to the patient. Adding the moisture to the mixing gas allows for the use of many standard gas-moisturizing techniques such as ultrasonics, heat, venturi, cavitation, convection (wicking) or others. See, e.g., U.S. Pat. No. 6,062,212, which describes a piezoelectric transducer to atomize droplets of liquid for dispensing pharmaceutical preparations, the contents of which are hereby incorporated by reference as if recited in full herein. For example, the hyperpolarized gas may be moisturized by using a piezoelectric dispensing member having a liquid reservoir, a vibrating substrate, and an outlet that is in fluid communication with the hyperpolarized noble gas flow path. The piezoelectric member can be actuatable to vibrate the substrate (onto which moisture may be meted in desired quantities) and disperse moisture layered thereon to thereby introduce droplets of moisture into the hyperpolarized gas as the hyperpolarized gas is flowing along the travel path.

In any event, the moisture can be added to conventional hyperpolarized gas administration protocols and sufficiently controlled without negatively influencing the polarization process.

In addition, because the polarization level of polarized gas can be degraded more quickly in the presence of moisture and other gases, the moisture and mixing can be performed proximate in time to the administration, in situ, and just prior to inhalation to reduce the polarization degradation which may be induced. An additional advantage to the use of moisture prior to inhalation is that it can act as an alkali metal scavenger to provide additional filtering of the alkali metal prior to administration to the subject if such residue was present in the formulation.

Embodiment 3

In-line Delivery Moisture Cartridge

The delivery of the polarized gas dose to a patient may provide a desirable opportunity time to introduce moisture to the polarized gas. This is because the exposure time of the polarized gas with the moisture is short and therefore has a relatively limited opportunity to substantially deteriorate the polarization level. As such, in certain embodiments, a moisture cartridge 75 in fluid communication with, and configured to dispense or add moisture to, flowing hyperpolarized gas during administration to a subject may be employed.

Figure 3:
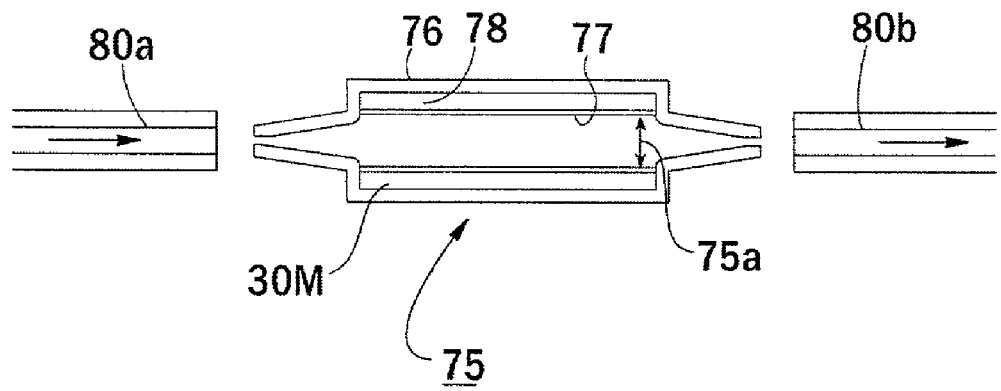
FIG. 3 is a front partial cutaway view of a device for moisturizing or humidifying polarized gas according to embodiments of the present invention.

FIG. 3 illustrates one suitable way in which moisture can be added during delivery by flowing the dry hyperpolarized gas through an in-line moisture cartridge 75: The cartridge 75 can be configured to sealably mate with flow conduit 80a, 80b so as to provide a flowable lumen 75a therethrough. The cartridge 75 includes an outer wall 76 and an inner vapor permeable membrane 77 which defines a chamber 78 therebetween. The chamber 78 is configured to hold a quantity of liquid which generates the vapor or moisture 30M which is applied to the hyperpolarized gas as it travels through the lumen 75a of the cartridge 75. The vapor permeable membrane can be formed of or comprise a material which allows water vapor to pass therethrough. One example of a suitable material is expanded polypropylene (and, as an example, GORE-TEX material). Moisture content may be controlled by the surface area of the walls of the lumen 75a. That is, the length (L) and diameter (D) of the permeable membrane which defines the inner lumen 75a can be configured to provide the desired contact surface exposure to the gas traveling through the cartridge 75. A larger surface area (i.e., L and/or D) and/or flow rate can impact the amount of moisture and humidification applied to the hyperpolarized gas as it travels through the cartridge 75. In certain embodiments, the cartridge 75 can be configured to be inserted in the inhalation delivery line proximate the inhalation mask or the administration site of the subject such that the moisture is applied just prior and proximate in time to the gas being inhaled by the subject. Other dispensing or moisturizing configurations or mechanisms can also be employed, as discussed above, such as, but not limited to, an ultrasonic mechanism, a piezoelectronic or piezoceramic vibrating mechanism, a venturi mixing mechanism, a wicking mechanism, and the like.

Embodiment 4

Endogenous Moisturizer "Re-Breather" Summary

Figure 4:
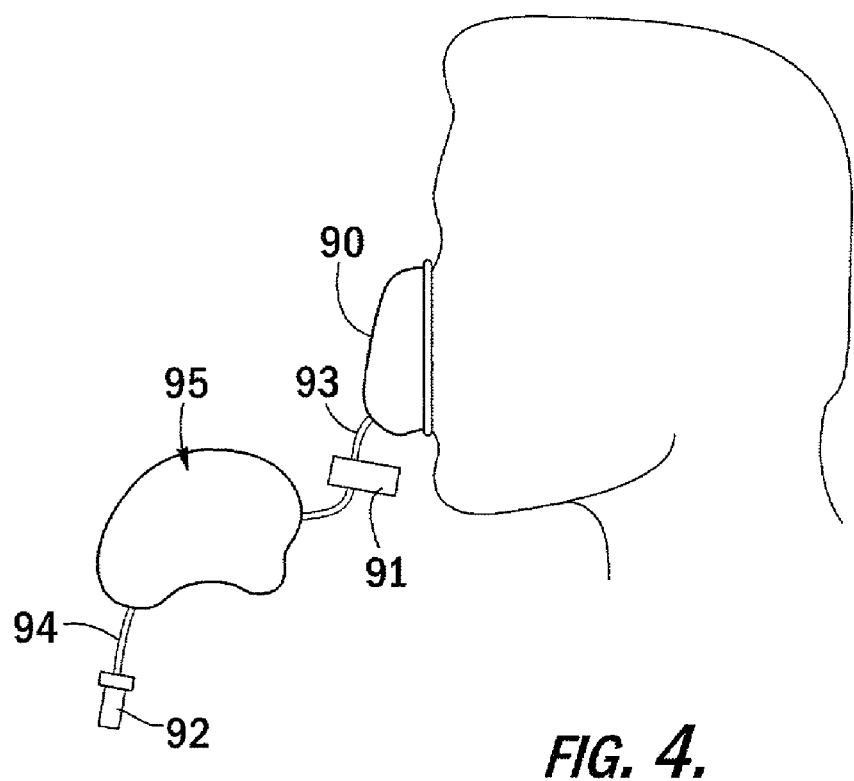
FIG. 4 is a schematic illustration of a delivery accessory used to moisturize the hyperpolarized gas proximate inhalation according to embodiments of the present invention.

As shown in FIG. 4, a breathing mask 90 can be attached to the patient dose bag. The patient is then instructed to exhale one or more times proximate in time to or just prior to polarized gas delivery. The mask 90 can be formed of material which traps or increases the amount of captured moisture during exhalation and which is also friendly to the polarized gas which will travel therethrough (polymers, plastic, and the like). Moisture from the exhaled breath (typically at above about >90% RH) will condense on the inner surface of the mask. As the polarized gas is subsequently inhaled, sufficient moisture can be transferred to the gas to provide the desired RH of typically about 10-30%, and preferably, at about at least 30% for comfortable breathing, according to embodiments of the present invention.

Alternately, a porous, low-density filter material can be attached to the inside of the mask 90 (such as, but not limited to, a flocked lining for a garment (not shown)) or placed in a small canister at the end of the patient delivery tube 93 (no mask would be required in this case) for the polarized gas. This may increase the surface area for condensation of water vapor from the exhaled breath without significantly increasing breathing resistance. Two one-way check valves 91, 92 can be positioned on the flow lines 93, 94, to inhibit exhaled breath from entering the hyperpolarized gas bag 95 and to keep air from entering the exhaust vent during inhalation. Suitable gas bag containers are described in U.S. Pat. No. 6,128,918, the contents of which are hereby incorporated by reference. This reference also discusses suitable materials for forming gas-contacting substances, such as for the inner surface of the mask 90, for inhibiting contact induced relaxation.

Embodiment 5

Bubbling

Figure 5:
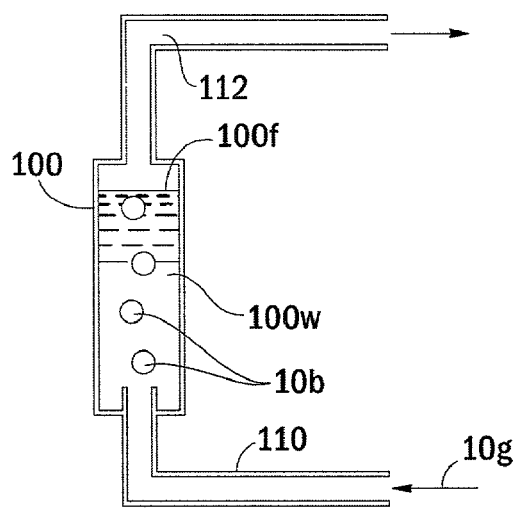
FIG. 5 is a schematic illustration of certain embodiments of the present invention for adding moisture to the hyperpolarized gas according to the present invention.

Turning now to FIG. 5, a closed water tank 100 is shown with a level of liquid such as water 100w (the liquid can be any suitable bio-compatible substance that inhibits the depolarization of the gas) held therein. The free surface 100f of the liquid (which shall be described as water for ease of discussion) is such that it resides proximate but below a top portion of the water tank 100. A gas flow tube 110 is configured to direct hyperpolarized gas into the water tank 100. As shown, the gas flow tube 110 is arranged to direct the gas in from the bottom of the tank 100.

In operation, a quantity of hyperpolarized gas 10g is released out of the gas flow tube 110 located tube at the bottom of the closed water tank 100. Other configurations of gas flow tubes can also be employed, such as one where the inlet tube 110 is oriented to first be at a level above the water level and then oriented to travel down a distance to enter at a side or lower portion of the tank (not shown).

As shown, bubbles of hyperpolarized gas 10b are created and move upward to the surface 100f. Moisturization of the hyperpolarized gas occurs as the gas travels through the fluid, arrives at the surface of the bubbles, and is released above the free surface of water. The gas is then exposed to the vapor above the surface level according to the vapor pressure of water at the temperature and pressure conditions of the tank. An outgoing tube 112 directs the moisturized hyperpolarized gas to flow out or downstream thereof.

In certain embodiments, the water in the tank 100 can be heated, which can increase the moisture content of the hyperpolarized gas. In the embodiment shown in FIG. 5, the pressure of the incoming and outgoing flow of hyperpolarized gas can be regulated, which can modify the amount of water in the vapor phase above the free surface of water in the tank, and which can also modify the size of the gas bubbles 10b. It is noted that both, or either, of heat and pressure regulation can be used (at the same time or at different times) to regulate the quantity of moisture added to the flow of hyperpolarized gas in this embodiment as well as other embodiments described herein. The gas flow tube 110 can also be configured with a nozzle or outlet port to help generate bubbles of a desired size.

As noted above, the gas contacting surface materials can be chosen so that polarization loss due to material surfaces is inhibited.

Embodiment 6

Parallel Addition of Polarized Gas and Moisture Orally In Situ

Figure 6:
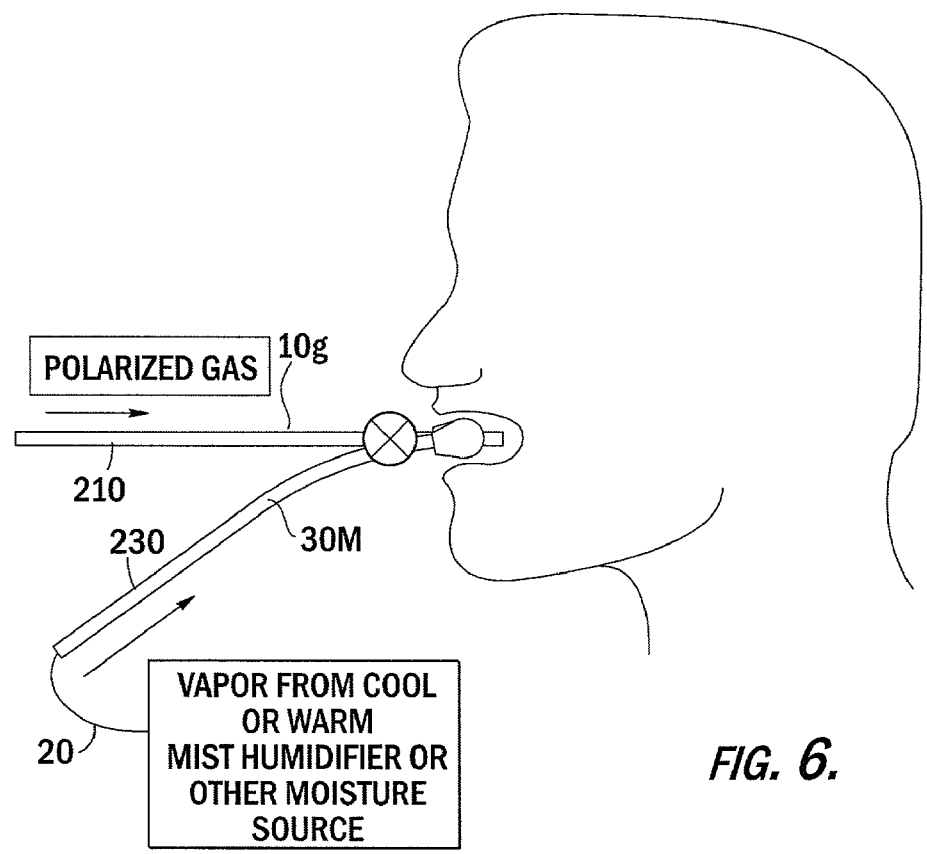
FIG. 6 is a schematic illustration of yet another embodiment for methods and devices adding moisture to hyperpolarized gas according to the present invention.

Adding moisture at the inhalation point in the administration process allows a reduced amount of exposure of polarized gas to moisture prior to imaging and thus inhibits the opportunities for polarization loss. FIG. 6 illustrates that the polarized gas 10g can be hydrated by directing the polarized gas to mix with moisture 30M in the mouth and/or throat. Such a delivery can reduce the polarized gas' contact with moisture and may also reduce throat irritation. As shown, separate conduit or delivery lines 210, 230 can be used to direct the gas 10g and vapor from the moisturizer 20 into the subject (for oral delivery whether into to one or more of the mouth, nasal cavity, or throat). The two lines 210, 230 can be held together in alignment by a coupler 240 and may include a releasable valve or flow control means positioned upstream 250 thereof for concurrently activating or controlling the flow of the vapor and gas into the subject. Such a valve or flow control means may include a pressure fit clamp sized to close the conduits 210, 230 to stop flow and to open to allow flow. The flow rates of each line 210, 230 may be separately controlled to provide the desired moisture content. The vapor can be combined with the mixer or buffer gas as noted above and introduced in situ orally in the subject via line 230. The moisturizer vapor can be supplied from a cool or warm mist humidifier or other suitable moisturized vapor source.

Embodiment 7

Wick Moisture into Polarized Gas Stream

Figure 7:
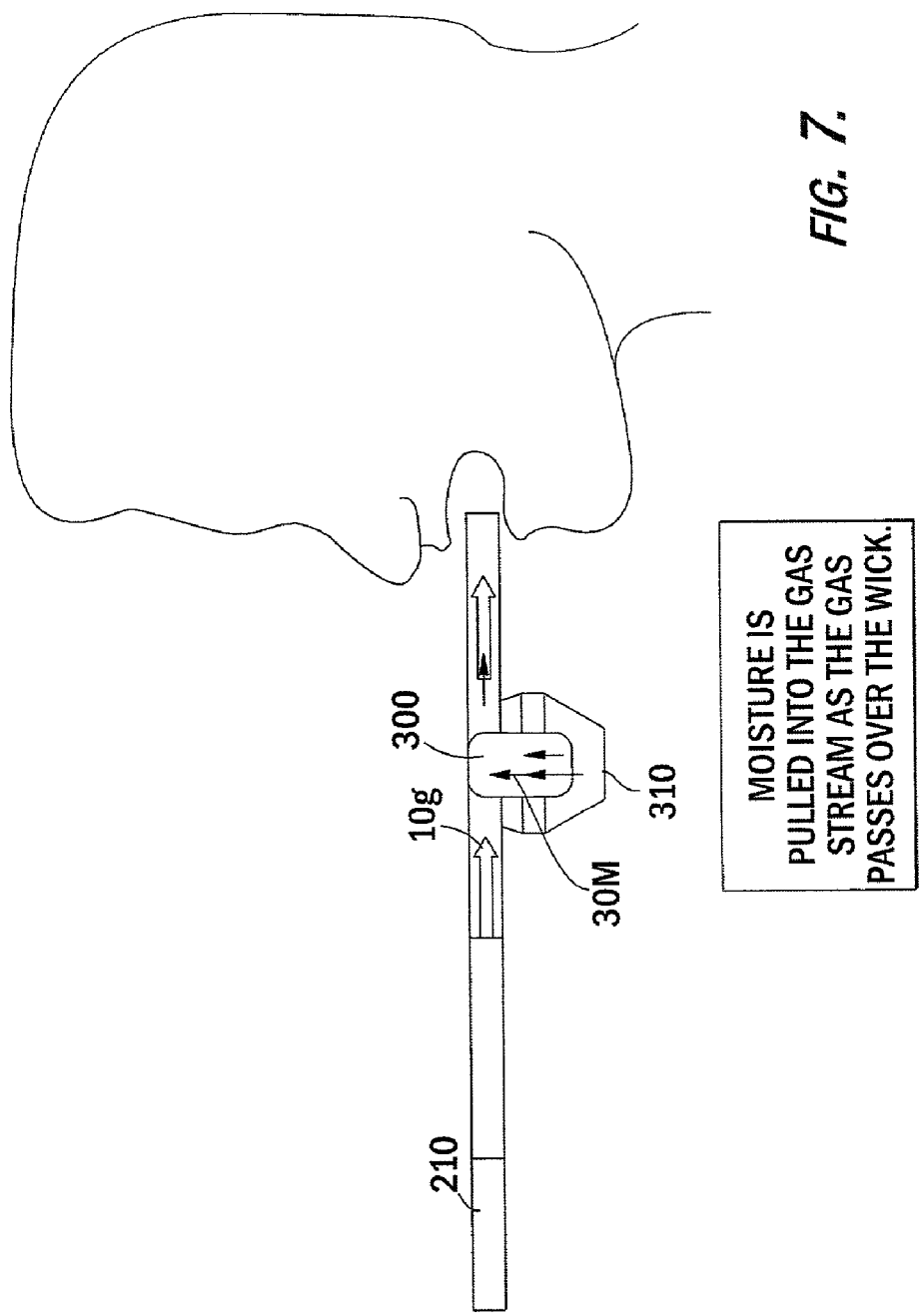
FIG. 7 is a schematic illustration of additional embodiments of methods and devices for adding moisture to hyperpolarized gas according to embodiments of the present invention.

As shown in FIG. 7, the polarized gas can be hydrated or moisturized with at least one wick 300. As shown, the wick 300 has two opposing end portions, one of which resides in a liquid bath 310, and the other of which extends, at least partially, into the flow path of the hyperpolarized gas 10g. The wick 300 is configured and sized such that it absorbs liquid from the liquid bath 310. The wet wick 300 then extends into the flow path and the hyperpolarized gas is exposed to the wet wick 300 as it travels along the inhalation flow path. As such, the wick 300 is configured to draw or pull or direct moisture via capillary action into the inhalation path or tube as the gas flows thereabout. In certain embodiments, this action can occur during inhalation. That is, the gas flow can be induced by the inhalation of the subject and the moisture added as the gas flows over the wick(s).

The wick 300 and liquid bath 310 can be configured to sealably engage with the inhalation tube or conduit 210 to provide an air-tight engagement therewith. The wick 300 can be a plurality of wicks configured to provide sufficient surface area to introduce the desired moisture content into the gas stream. The wick 300 can be formed of materials selected for their ability to provide the desired capillary action and ability to transfer moisture while being substantially non-depolarizing to the hyperpolarized gas. In addition, the wick(s) 300 can be sized and configured to allow axial gas flow (to avoid substantially impeding the flow of the gas) while imparting sufficient moisture.

This embodiment can reduce the amount of time that the polarized gas is in contact with moisture and may also reduce throat irritation over dry delivery while also providing a relatively non-complex device for allowing the moisturized inhalation.

The present invention finds use for both veterinary and medical applications. The present invention may be advantageously employed for diagnostic evaluation and/or treatment of subjects, in particular human subjects, because it may be safer (e.g., less toxic) than other methods known in the art (e.g., radioactive methods). Subjects according to the present invention can be any animal subject, and are preferably mammalian subjects (e.g., humans, canines, felines, bovines, caprines, ovines, equines, rodents, porcines, and/or lagomorphs), and more preferably are human subjects.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, where used, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An apparatus for adding moisture to hyperpolarized noble gas product suitable for in vivo administration, comprising:
   a hyperpolarized noble gas supply source providing the dose of hyperpolarized noble gas required for an imaging session;
   an enclosed gas flow path extending between the hyperpolarized noble gas supply source and an oral cavity for a subject;
   means for flowing, under pressure, a quantity of hyperpolarized noble gas along the gas flow path;
   means for introducing moisture to a quantity of gaseous phase hyperpolarized noble gas in fluid communication with the hyperpolarized noble gas supply source, said means for introducing moisture being located between the hyperpolarized noble gas supply source and the subject; and
   means for generating a moisturized pharmaceutical grade gaseous hyperpolarized noble gas product which is suitable for inhalation or ventilation administration to a subject, wherein said introducing means is configured so as to moisturize in situ while the hyperpolarized gas is flowing along the gas flow path, so that the moisture is introduced at or in advance of the oral cavity of the subject;
   said apparatus configured such that said enclosed gas flow path only conducts the moisture and the hyperpolarized noble gas therealong.

2. An apparatus according to claim 1, wherein said means for introducing moisture is configured such that the pharmaceutical hyperpolarized gas product has a relative humidity of between about 5-80%.

3. An apparatus according to claim 2, wherein the relative humidity is between about 10-30%.

4. An apparatus according to claim 1, wherein the means for introducing comprises a moisturizer cartridge positioned in the gas flow path, wherein the cartridge includes a liquid vapor permeable membrane with an outside wall holding a quantity of captured liquid therein, and wherein, in operation, moisture is introduced to the hyperpolarized noble gas through the permeable membrane as the gas travels along the gas flow path.

5. An apparatus according to claim 1, wherein said introducing means is configured to flow water vapor into the flow path of the hyperpolarized gas in advance of the subject end of the gas flow path such that the hyperpolarized gas is flowably moisturized in advance of the oral cavity of the subject.

6. An apparatus according to claim 2, wherein said introducing means comprises a liquid filled reservoir tank having a gas entry port and a gas exit port, the gas entry port being in fluid communication with the hyperpolarized gas supply source, wherein, in operation, the hyperpolarized gas is directed to enter the reservoir through the entry port, to then bubble up through the liquid held in the liquid reservoir tank, and exit the gas exit port.

7. An apparatus according to claim 1, wherein the introducing means employs moisture generated from water vapor.

8. An apparatus according to claim 1, wherein the introducing means employs an aqueous mixture comprising deoxygenated water.

9. An apparatus according to claim 1, further comprising heating means for heating the hyperpolarized gas prior to flowing it into the subject.

* * * * *